(12) United States Patent
Pazhianur et al.

(10) Patent No.: US 8,653,001 B2
(45) Date of Patent: Feb. 18, 2014

(54) AGRICULTURAL ADJUVANT COMPOSTIONS, PESTICIDE COMPOSITIONS, AND METHODS FOR USING SUCH COMPOSITIONS

(75) Inventors: Rajesh Pazhianur, Yardley, PA (US); Hedieh Modaressi, Princeton, NJ (US); Francis George Smith, Robbinsville, NJ (US)

(73) Assignee: Rhodia Operations, Aubervilliers (FR)

( * ) Notice: Subject to any disclaimer, the term of this patent is extended or adjusted under 35 U.S.C. 154(b) by 1359 days.

(21) Appl. No.: 11/598,929

(22) Filed: Nov. 14, 2006

(65) Prior Publication Data

US 2007/0155628 A1 Jul. 5, 2007

Related U.S. Application Data

(60) Provisional application No. 60/736,610, filed on Nov. 14, 2005.

(51) Int. Cl.
*A01N 57/18* (2006.01)

(52) U.S. Cl.
USPC .......................................................... 504/205

(58) Field of Classification Search
None
See application file for complete search history.

(56) References Cited

U.S. PATENT DOCUMENTS

| | | |
|---|---|---|
| 3,225,074 A | 12/1965 | Cowen et al. |
| 3,527,593 A | 9/1970 | Bland et al. |
| 3,723,357 A | 3/1973 | Hansen |
| 3,882,051 A | 5/1975 | Hansen |
| 4,011,388 A | 3/1977 | Murphy et al. |
| 4,107,328 A | 8/1978 | Michaels |
| 4,117,107 A | 9/1978 | Shapiro |
| 4,122,159 A | 10/1978 | Madrange et al. |
| 4,137,191 A | 1/1979 | Lohr |
| 4,243,549 A | 1/1981 | Messenger et al. |
| 4,452,732 A | 6/1984 | Bolich, Jr. |
| 4,477,365 A | 10/1984 | Verboom et al. |
| 4,585,846 A | 4/1986 | Schulz et al. |
| 4,607,076 A | 8/1986 | Schulz et al. |
| 4,650,848 A | 3/1987 | Schulz et al. |
| 4,703,797 A | 11/1987 | Djabbarah |
| 4,708,998 A | 11/1987 | Schulz et al. |
| 4,742,135 A | 5/1988 | Schulz et al. |
| 4,788,247 A | 11/1988 | Schulz et al. |
| 4,822,847 A | 4/1989 | Schulz et al. |
| 4,831,092 A | 5/1989 | Bock et al. |
| 4,835,234 A | 5/1989 | Valint et al. |
| 4,882,405 A | 11/1989 | Schulz et al. |
| 4,996,045 A | 2/1991 | Leighton et al. |
| 5,153,289 A | 10/1992 | Schulz et al. |
| 5,164,120 A | 11/1992 | Borland et al. |
| 5,180,414 A | 1/1993 | Darchy et al. |
| 5,258,358 A | 11/1993 | Kocur et al. |
| 5,292,942 A | 3/1994 | Aigner et al. |
| 5,338,793 A | 8/1994 | Loftin |
| 5,341,932 A | 8/1994 | Chen et al. ................. 206/524.7 |
| 5,354,906 A | 10/1994 | Weitmeyer et al. |
| 5,385,206 A | 1/1995 | Thomas |
| 5,439,317 A | 8/1995 | Bishop et al. |
| 5,464,806 A | 11/1995 | Kassebaum et al. |
| 5,551,516 A | 9/1996 | Norman et al. |
| 5,580,856 A | 12/1996 | Prestrelski et al. ............. 514/21 |
| 5,612,285 A | 3/1997 | Arnold |
| 5,686,400 A | 11/1997 | Urfer et al. |
| 5,700,760 A | 12/1997 | Magin et al. |
| 5,703,016 A | 12/1997 | Magin et al. |
| 5,747,416 A | 5/1998 | Mc Ardle et al. ............. 504/115 |
| 5,863,863 A | 1/1999 | Hasebe et al. ................ 504/116 |
| 5,874,394 A | 2/1999 | Thomas et al. |
| 5,877,143 A | 3/1999 | Abbas et al. |
| 5,888,934 A | 3/1999 | Townson et al. |
| 5,897,699 A | 4/1999 | Chatterji et al. |
| 5,912,209 A | 6/1999 | Kassebaum et al. .......... 504/206 |
| 5,985,798 A | 11/1999 | Crudden |
| 5,998,332 A | 12/1999 | Sato et al. ..................... 504/127 |
| 6,030,928 A | 2/2000 | Stahl et al. |
| 6,036,638 A | 3/2000 | Nwawka |
| 6,127,318 A | 10/2000 | Sato et al. |
| 6,165,939 A | 12/2000 | Agbaje et al. |
| 6,210,476 B1 | 4/2001 | Chatterji et al. |
| 6,284,854 B1 | 9/2001 | Bowers et al. |
| 6,288,010 B1 | 9/2001 | Rose et al. |
| 6,302,209 B1 | 10/2001 | Thompson et al. |
| 6,329,322 B1 | 12/2001 | Reierson |
| 6,346,588 B1 | 2/2002 | Fench et al. |
| 6,369,122 B1 | 4/2002 | Subramanyam |

(Continued)

FOREIGN PATENT DOCUMENTS

| | | |
|---|---|---|
| CA | 2554335 | 8/2005 |
| EP | 0373851 | 6/1990 |

(Continued)

OTHER PUBLICATIONS

Ullmann's Encyclopedia of Industrial Chemistry, 5th Ed., vol. A 10, Edited by Gerhartz et al., pp. 176-177, Wiley-VCH Verlag GmbH & Co. KGaA, Weinheim, Germany, May 5, 1994.

(Continued)

*Primary Examiner* — Alton Pryor

(57) ABSTRACT

An adjuvant composition that contains, based on 100 parts by weight of the adjuvant composition (a) one or more betaine surfactant compounds, and (b) one or more surfactant compounds selected from, alkyl ether sulfates, sulfonates, sulfosuccinates, alkyl ether carboxylates, alkoxylated fatty acids, and alkoxylated alcohols is useful as a component of pesticide compositions.

4 Claims, No Drawings

(56) References Cited

U.S. PATENT DOCUMENTS

| | | | |
|---|---|---|---|
| 6,376,566 B1 | 4/2002 | Bergeron et al. | |
| 6,407,042 B1 | 6/2002 | Ward et al. | |
| 6,417,268 B1 | 7/2002 | Zhang et al. | |
| 6,432,878 B1 | 8/2002 | Brigance | 504/206 |
| 6,432,884 B1 | 8/2002 | Lachut | 504/363 |
| 6,451,731 B1 | 9/2002 | Agbaje et al. | |
| 6,500,784 B1 | 12/2002 | Mille et al. | 504/206 |
| 6,566,408 B1 | 5/2003 | Cotrell et al. | |
| 6,642,178 B2 | 11/2003 | Woznica et al. | |
| 6,645,912 B1 | 11/2003 | Mille et al. | |
| 6,645,914 B1 | 11/2003 | Woznica et al. | 504/206 |
| 6,653,257 B2 | 11/2003 | Mille et al. | 504/206 |
| 6,770,268 B1 | 8/2004 | Hall et al. | |
| 6,770,594 B2 | 8/2004 | Bickers et al. | 504/212 |
| 6,831,108 B2 | 12/2004 | Dahanayake et al. | |
| 6,881,707 B2 | 4/2005 | Howat et al. | |
| 6,992,046 B2 | 1/2006 | Bramati et al. | 504/206 |
| 7,135,437 B2 | 11/2006 | Pallas et al. | |
| 7,316,990 B2 | 1/2008 | Tank et al. | |
| 8,236,730 B2 | 8/2012 | Bramati et al. | |
| 8,383,137 B2 | 2/2013 | Modaressi et al. | |
| 2002/0187917 A1 | 12/2002 | Lazarowitz | |
| 2003/0045431 A1 | 3/2003 | Mille et al. | |
| 2003/0118540 A1 | 6/2003 | Charlton et al. | |
| 2003/0158042 A1 | 8/2003 | Bramati et al. | |
| 2004/0097372 A1 | 5/2004 | Abraham et al. | |
| 2004/0110644 A1 | 6/2004 | Halliday et al. | |
| 2004/0121917 A1 | 6/2004 | Pakulski | |
| 2005/0003965 A1 | 1/2005 | Xiao et al. | |
| 2005/0010009 A1 | 1/2005 | Schulz et al. | |
| 2005/0020454 A1 | 1/2005 | Francini et al. | |
| 2005/0130842 A1 | 6/2005 | Fleute-Schlachter et al. | |
| 2005/0170965 A1 | 8/2005 | Bramati et al. | |
| 2006/0019830 A1 | 1/2006 | Xu et al. | |
| 2006/0060354 A1 | 3/2006 | Lewis et al. | |
| 2006/0264328 A1 | 11/2006 | Modaressi et al. | 504/165 |
| 2007/0155628 A1 | 7/2007 | Pazhianur et al. | |
| 2007/0282075 A1 | 12/2007 | Koch et al. | |
| 2008/0103047 A1 | 5/2008 | Gioia et al. | |
| 2008/0312083 A1 | 12/2008 | Gioia | |
| 2009/0018018 A1 | 1/2009 | Gioia et al. | |
| 2010/0069269 A1 | 3/2010 | Prat et al. | |
| 2010/0093874 A1 | 4/2010 | Monin et al. | |
| 2010/0140531 A1 | 6/2010 | Prat et al. | |
| 2011/0009269 A1 | 1/2011 | Gioia et al. | |
| 2011/0015071 A1 | 1/2011 | Kisenwether et al. | |
| 2012/0040833 A1 | 2/2012 | Kisenwether et al. | |
| 2012/0165195 A1 | 6/2012 | Iskandar et al. | |

FOREIGN PATENT DOCUMENTS

| | | | |
|---|---|---|---|
| EP | 0274369 | | 9/1990 |
| EP | 0 483 095 A2 | | 10/1991 |
| EP | 0511611 A1 | | 4/1992 |
| EP | 0370338 | | 5/1992 |
| EP | 0508022 | | 10/1992 |
| EP | 0573118 | | 12/1993 |
| EP | 0449159 | | 7/1995 |
| EP | 0810239 | | 9/2000 |
| EP | 1541023 A2 | | 11/2004 |
| FR | 2 398 797 | | 7/1978 |
| JP | 10 183176 | | 3/1987 |
| JP | 11-349826 | | 6/1998 |
| WO | 9212637 | | 8/1992 |
| WO | 92/14907 | | 9/1992 |
| WO | WO 97/01281 | * | 1/1997 |
| WO | 9706230 | | 2/1997 |
| WO | 97/36489 | | 10/1997 |
| WO | 98/14060 | | 4/1998 |
| WO | 99/03895 | | 1/1999 |
| WO | 99/15610 | | 4/1999 |
| WO | WO 01/08482 | * | 7/1999 |
| WO | WO 99/45780 | | 9/1999 |
| WO | 99/62338 | | 12/1999 |
| WO | 0038523 | | 7/2000 |
| WO | WO 00/38523 | | 7/2000 |
| WO | 0067571 | | 11/2000 |
| WO | 0067573 | | 11/2000 |
| WO | 0108482 | | 2/2001 |
| WO | WO 01/08482 A1 | | 2/2001 |
| WO | WO 01/17358 A1 | | 3/2001 |
| WO | 0126469 | | 4/2001 |
| WO | WO 01/26463 A1 | | 4/2001 |
| WO | WO 0126463 | * | 4/2001 |
| WO | 0189302 | | 11/2001 |
| WO | 02/26036 | | 4/2002 |
| WO | 03/049813 | | 6/2003 |
| WO | 03063589 A2 | | 8/2003 |
| WO | 2004/107861 | | 12/2004 |
| WO | 2006035983 A1 | | 4/2006 |
| WO | 2006069791 A1 | | 7/2006 |
| WO | 2006069794 A2 | | 7/2006 |
| WO | WO 2006/069791 A1 | | 7/2006 |
| WO | WO 2006/069794 A2 | | 7/2006 |
| WO | 2006124606 A2 | | 11/2006 |
| WO | WO 2007/054540 A2 | | 5/2007 |

OTHER PUBLICATIONS

"Application Guide for Household & Industrial Markets"; McIntyre Group Ltd., Copyright 2002, (Jan. 2003), obtained online @ http://www.dewolfchem.com/pdf/Mcintyre_HI&I_Application_Guide.pdf, (downloaded Mar. 6, 2012).

Basheva et al.; Role of Betaine as Foam Booster in the Presence of Silicone Oil Drops; Langmuir 2000, 16, 1000-1003; Received Jun. 16, 1999; 2000 American Chemical Society Published on Web Dec. 8, 1999.

* cited by examiner

AGRICULTURAL ADJUVANT COMPOSTIONS, PESTICIDE COMPOSITIONS, AND METHODS FOR USING SUCH COMPOSITIONS

This application claims the benefit of Provisional Application No. 60/736,610 filed Nov. 14, 2005

FIELD OF THE INVENTION

This invention relates to agricultural adjuvant compositions, pesticide compositions, and methods for using such compositions.

BACKGROUND OF THE INVENTION

Many agricultural pesticides, including insecticides, fungicides, herbicides, miticides, and plant growth regulators, are applied in the form of a liquid composition. In addition to the pesticide and a solvent, such liquid compositions typically include one or more adjuvant compounds intended to improve one or more properties of the liquid composition, such as for example, storage stability, ease of handling, pesticide efficacy against target organisms.

There is a continuing interest in pesticide compositions that exhibit improved properties.

SUMMARY OF THE INVENTION

In a first aspect, the present invention is directed to an adjuvant composition comprising,
(a) one or more betaine surfactant compounds, and
(b) one or more surfactant compounds selected from alkyl ether sulfates, sulfonates, sulfosuccinates, alkyl ether carboxylates, alkoxylated fatty acids, and alkoxylated alcohols.

In a second aspect, the present invention is directed to a pesticide composition, comprising:
(a) one or more betaine surfactant compounds,
(b) one or more surfactant compounds selected from alkyl ether sulfates, sulfonates, sulfosuccinates, alkyl ether carboxylates, alkoxylated fatty acids, and alkoxylated alcohols, and
(c) an effective amount of a pesticide.

In a third aspect, the present invention is directed to a method for treating a target plant, comprising applying the above described pesticide composition to such plant.

DETAILED DESCRIPTION OF INVENTION AND PREFERRED EMBODIMENTS

As used herein, the term "alkyl" means a saturated straight chain, branched chain, or cyclic hydrocarbon radical, such as for example, methyl, ethyl, n-propyl, iso-propyl, n-butyl, sec-butyl, t-butyl, pentyl, n-hexyl, and cyclohexyl.

As used herein, the term "alkoxy" means an oxy radical that is substituted with an alkyl group, such as for example, methoxy, ethoxy, propoxy, isopropoxy, and butoxy. As used herein in reference to an organic compound, the term "alkoxylated" means that the compound comprises one or more alkoxy or, more typically, poly(alkyleneoxy) moieties, such as, for example a poly(ethyleneoxy), poly(propyleneoxy), or poly(ethlyeneoxypropyleneoxy) moiety and the term "ethoxylated" means that the compound comprises at least one ethoxy or poly(ethyleneoxy) moiety. As used herein in reference to a poly(alkyleneoxy) moiety, the notation "(n)", wherein n is an integer, indicates the number of alkyleneoxy monomeric units in the poly(alkyleneoxy) moiety. For example such as "ethoxylated (15) tridecyl alcohol" means a tridecyl alcohol ethoxylated with 15 moles of ethyleneoxy units per mole of tridecyl alcohol.

As used herein, the term "alkenyl" means an unsaturated straight chain, branched chain, or cyclic hydrocarbon radical that contains one or more carbon-carbon double bonds, such as, for example, ethenyl, 1-propenyl, and 2-propenyl.

As used herein, the term "aryl" means a monovalent unsaturated hydrocarbon radical containing one or more six-membered carbon rings in which the unsaturation may be represented by three conjugated double bonds, which may be substituted one or more of carbons of the ring with hydroxy, alkyl, alkenyl, halo, haloalkyl, or amino, such as, for example, phenoxy, phenyl, methylphenyl, dimethylphenyl, trimethylphenyl, chlorophenyl, trichloromethylphenyl, aminophenyl, and tristyrylphenyl.

As used herein, the term "arylene" means a divalent unsaturated hydrocarbon radical containing one or more six-membered carbon rings in which the unsaturation may be represented by three conjugated double bonds, which may be substituted one or more of carbons of the ring with hydroxy, alkyl, alkenyl, halo, haloalkyl, or amino, such as, for example, phenylene, methylphenylene, trimethylphenylene, aminophenylene, and tristyrylphenylene.

As used herein, the term "aralkyl" means an alkyl group substituted with one or more aryl groups, such as, for example, phenylmethyl, phenylethyl, and triphenylmethyl.

As used herein, the term "aralkenyl" means an alkenyl group substituted with an aryl group, such as, for example, phenylethenyl, and phenylpropenyl.

As used herein, the term "aryloxy" means an oxygen radical substituted with an aryl group, such as, for example, phenoxy, methylphenoxy, and trimethylphenoxy.

As used herein, the terminology "($C_n$-$C_m$)" in reference to an organic group, wherein n and m are each integers, indicates that the group may contain from n carbon atoms to m carbon atoms per group.

As used herein, the term "agronomically acceptable salts" refers to salts prepared from agronomically acceptable non-toxic bases or acids including inorganic or organic bases and inorganic or organic acids. Typical agronomically acceptable salts the compound referred to herein comprise an anion derived from the compound, for example, by deprotonation of a hydroxy or hydroxyalkyl substituent, and one or more positively charged counterions. Suitable positively charged counterions include inorganic cations and organic cations, such as for example, sodium cations, potassium cations, calcium cations, magnesium cations, isopropylamine cations, ammonium cations, and tetraalkylammonium cations.

Betaine surfactant compounds are generally known compounds. In one embodiment, the betaine surfactant compound comprises one or more compounds according to formula (I):

wherein:
$R^1$, $R^2$, and $R^3$ are each independently alkyl, hydroxyalkyl, alkylamidoalkyl, or —$CH_2COOH$,
or an agronomically acceptable salt thereof.

In one embodiment, $R^1$ and $R^2$ are each independently $(C_1-C_6)$alkyl, more typically methyl, and $R^3$ is $(C_1-C_{30})$alkyl, more typically $(C_8-C_{18})$alkyl.

In one embodiment, $R^1$ and $R^2$ are each independently $(C_1-C_6)$alkyl, more typically methyl, and $R^3$ is alkylamidoalkyl, more typically $(C_1-C_{30})$alkylamido$(C_1-C_6)$alkyl.

Suitable betaines include, for example, decyl dimethyl betaine, lauryl dimethyl betaine, coco dimethyl betaine, stearyl dimethyl betaine, cocoamidopropyl betaine, and mixtures thereof.

Alkyl ether sulfate surfactant compounds are generally known compounds and include agronomically acceptable salts of alkoxylated alkyl sulfates. In one embodiment, the adjuvant composition comprises one or more alkyl ether sulfate surfactant compounds according to formula (II):

$$R^5-O-\left[\underset{\underset{H_2}{|}}{HC}-\underset{}{C}-O\right]_m-\underset{\underset{O}{\parallel}}{\overset{\overset{O}{\parallel}}{S}}-O^--X^+ \quad (II)$$

with $R^4$ on the HC carbon.

wherein:
each $R^4$ is independently H or methyl,
$R^5$ is alkyl,
m is an integer of from 1 to 100, more typically from 1 to 50, and
$X^+$ is an agronomically acceptable cation.

In one embodiment, $R^5$ is $(C_1-C_{30})$alkyl, more typically $(C_8-C_{18})$alkyl.

In one embodiment, each $R^4$ is H and is from 1 to about 10.

Suitable alkyl ether sulfate surfactant compounds, include, for example, sodium $(C_8-C_{10})$alkyl ether sulfate and sodium lauryl ether sulfate.

Sulfonate surfactant compounds are generally known compounds and include agronomically acceptable salts of mono-sulfonic acids, agronomically acceptable salts of di-sulfonic acids, and mixtures thereof. In one embodiment, the adjuvant composition comprises one or more sulfonate surfactant compounds according to formula (III) or (IV):

$$R^6-\underset{\underset{O}{\parallel}}{\overset{\overset{O}{\parallel}}{S}}-O^--X^+ \quad (III)$$

$$X^+ \, {}^-O-\underset{\underset{O}{\parallel}}{\overset{\overset{O}{\parallel}}{S}}-R^7-O-R^{7'}-\underset{\underset{O}{\parallel}}{\overset{\overset{O}{\parallel}}{S}}-O^- \, X^+ \quad (IV)$$

wherein:
$R^6$ is aryl, aryloxy, or alkenyl,
$R^7$ and $R^{7'}$ are each independently arylene, and
$X^+$ is an agronomically acceptable cation.

In one embodiment, $R^6$ is phenyl, $(C_8-C_{18})$alkylphenyl, or $(C_8-C_{18})$alkylphenoxy.

In one embodiment, $R^7$ and $R^{7'}$ are each $(C_8-C_{18})$alkylphenylene.

Suitable sulfonate surfactant compounds include, for example, calcium dodecylbenzene sulfonate, calcium octadecylphenyl sulfonate, sodium tridecyl benzene sulfonate, isopropylamine dodecyl benzene sulfonate, isopropylamine tridecyl benzene sulfonate, ammonium tridecyl phenyl sulfonate, sodium $(C_8-C_{18})$alkylphenoxysulfonate, sodium xylene sulfonate, sodium $(C_{14}-C_{16})$alpha olefin sulfonate, disodium alkyldiphenyloxide disulfonates such as, for example, DOWFAX 2A1 (Dow Chemical Company), and mixtures thereof.

Sulfosuccinate surfactant compounds are generally known compounds and include agronomically acceptable salts of mono-esters of sulfosuccinic acid, agronomically acceptable salts of di-esters of sulfosuccinic acid, each of which may, optionally, be alkoxylated, as well as mixtures thereof. In one embodiment, the adjuvant composition comprises one or more sulfosuccinate surfactant compounds according to formula (V):

$$\begin{array}{c} A \quad A' \\ O= \diagdown \diagup =O \\ | \\ O=S=O \\ | \\ O^- \, X^+ \end{array} \quad (V)$$

wherein:
A and A' are each independently $-O^-X^+$, or $$R^9-O-\left[\underset{\underset{R^8}{|}}{HC}-CH_2-O\right]_n-,$$

provided that at least one of A and A' is $$R^9-O-\left[\underset{\underset{R^8}{|}}{HC}-CH_2-O\right]_n-,$$

each $R^8$ is independently H or methyl,
each $R^9$ is independently H, alkyl, aryl, or alkylamidoalkyl,
each n is independently 0 or an integer of from 1 to about 100,
more typically from 1 to 50, and
each $X^+$ is an agronomically acceptable cation.

In one embodiment, one of A and A' is $-O^-X^+$, and the other of A and A' is $$R^9-O-\left[\underset{\underset{R^8}{|}}{HC}-CH_2-O\right]_n-,$$

wherein n is 0 or an integer of from 1 to about 20, and $R^9$ is $(C_6-C_{18})$alkyl, $(C_1-C_{18})$alkylphenyl, or $(C_6-C_{18})$alkylamido$(C_2-C_6)$alkyl.

In one embodiment, A and A' are each $$R^9-O-\left[\underset{\underset{R^8}{|}}{HC}-CH_2-O\right]_n-,$$

wherein each n is independently 0 or an integer of from 1 to about 20, and each $R^9$ is $(C_6-C_{18})$alkyl, $(C_1-C_{18})$alkylphenyl, or $(C_6-C_{18})$alkylamido$(C_2-C_6)$alkyl.

Suitable sulfosuccinicate surfactant compounds include, for example, disodium monooctylsulfosuccinate, sodium dioctylsulfosuccinate, disodium lauryl sulfosuccinate, disodium laureth sulfosuccinate, disodium laurimide (MEA) sulfosuccinate, disodium mono-alkylphenyl ether sulfosuccinate, and mixtures thereof.

Alkyl ether carboxylate surfactant compounds are generally known compounds and include agronomically acceptable salts of alkoxylated carboxylic acids. In one embodiment, the adjuvant composition comprises one or more alkyl ether carboxylate surfactant compounds according to formula (VI):

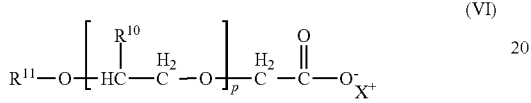

(VI)

wherein:
each $R^{10}$ is independently H or methyl,
$R^{11}$ is alkyl or alkenyl,
p is 0 or an integer of from 1 to 100, more typically an integer of from 1 to 50, and
$X^+$ is an agronomically acceptable cation.

In one embodiment, $R^{11}$ is $(C_8-C_{18})$alkyl.

In one embodiment, each $R^{10}$ is H and p is an integer of from 1 to about 10.

Suitable alkyl ether carboxylate surfactant compounds include, for example, sodium laureth-13 carboxylate.

In one embodiment, the adjuvant composition comprises one or more alkoxylated fatty acid surfactant compounds. The fatty acid portion of such alkoxylated fatty acid surfactant compounds is derived from a saturated or unsaturated mono- or di-fatty acids, typically $(C_6-C_{30})$ fatty acids, such as, for example, lauric acid, myristic acid, palmitic acid, stearic acid, oleic acid, linoleic acid, behenic acid, erucic acid, or a mixture thereof, including vegetable oils, such as, for example, tall oil, rapeseed oil, canola oil, soy oil, coconut oil, castor oil, corn oil, olive oil, sunflower oil, cottonseed oil, palm oil, peanut oil, sesame oil, safflower oil, linseed oil, flax seed oil, palm kernel oil, and mixtures thereof. These acids are alkoxylated with from 2 to 20 moles, more typically from 5 to 20 moles of a $(C_2-C_4)$alkylene oxide, more typically, ethylene oxide.

Alkoxylated alcohol surfactant compounds are generally known compounds. In one embodiment, the adjuvant composition comprises one or more alkoxylated alcohol surfactant compounds according to formula (VII):

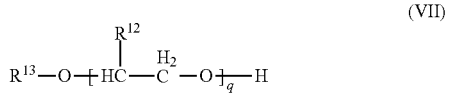

(VII)

wherein
each $R^{12}$ is independently H or methyl,
$R^{13}$ is alkyl or alkenyl,
q is an integer of from 1 to 100, more typically from 1 to 50, or an agronomically acceptable salt thereof.

In one embodiment, $R^{13}$ is $(C_6-C_{22})$alkyl.

In one embodiment, each $R^{12}$ is H and q is an integer of from 1 to about 30.

Suitable alkoxylated alcohol surfactant compounds include, for example, ethoxylated (15) tridecyl alcohol, ethoxylated (7) lauryl alcohol, ethoxylated (20) oleyl alcohol, ethoxylated (15) stearyl alcohol, and mixtures thereof.

The adjuvant composition comprises a non-zero amount of the one or more betaine surfactant compounds and a non-zero amount of one or more surfactant compounds selected from alkyl ether sulfates, sulfonates, sulfosuccinates, alkyl ether carboxylates, alkoxylated fatty acids, and alkoxylated alcohols. As used herein, "non-zero amount" means an amount greater than 0.

In one embodiment, the adjuvant composition comprises, based on 100 parts by weight ("pbw") of the adjuvant composition:
(a) greater or equal to than about 0.1 pbw, more typically from about 1 pbw to about 99 pbw, even more typically from about 1 pbw to about 50 pbw, and still more typically from about 5 pbw to about 25 pbw, of one or more betaine surfactant compounds, and
(b) greater or equal to than about 0.1 pbw, more typically from about 0.001 pbw to about 0.1 pbw, even more typically from about 0.005 pbw to about 0.095 pbw, and still more typically from about 0.02 pbw to about 0.08 pbw, of one or more surfactant compounds selected from alkyl ether sulfates, sulfonates, sulfosuccinates, alkyl ether carboxylates, alkoxylated fatty acids, and alkoxylated alcohols.

In one embodiment of the adjuvant composition, the one or more surfactants comprise at least one alkyl ether sulfate surfactant and may optionally further comprise one or more surfactants selected from sulfonates, sulfosuccinates, alkyl ether carboxylates, alkoxylated fatty acids, and alkoxylated alcohols.

In one embodiment of the adjuvant composition, the one or more surfactants comprise at least one sulfonate surfactant and may optionally further comprise one or more surfactants selected from alkyl ether sulfates, sulfosuccinates, alkyl ether carboxylates, alkoxylated fatty acids, and alkoxylated alcohols.

In one embodiment of the adjuvant composition, the one or more surfactants comprise at least one sulfosuccinate surfactant and may optionally further comprise one or more surfactants selected from alkyl ether sulfates, sulfonates, alkyl ether carboxylates, alkoxylated fatty acids, and alkoxylated alcohols.

In one embodiment of the adjuvant composition, the one or more surfactants comprise at least one alkyl ether carboxylate surfactant and may optionally further comprise one or more surfactants selected from alkyl ether sulfates, sulfonates, sulfosuccinates, alkoxylated fatty acids, and alkoxylated alcohols In one embodiment of the adjuvant composition, the one or more surfactants comprise at least one alkoxylated fatty acid surfactant and may optionally further comprise one or more surfactants selected from alkyl ether sulfates, sulfonates, sulfosuccinates, alkyl ether carboxylates, and alkoxylated alcohols In one embodiment of the adjuvant composition, the one or more surfactants comprise at least one alkoxylated alcohol surfactant and may optionally further comprise one or more surfactants selected from alkyl ether sulfates, sulfonates, sulfosuccinates, alkyl ether carboxylates, and alkoxylated fatty acids.

In one embodiment, the adjuvant composition comprises, per 1 pbw betaine component of such adjuvant composition, from about 0.1 to about 10, more typically from about 1 to about 8, and even more typically from about 2 to about 5 pbw, of one or more surfactant compounds selected from alkyl ether sulfates, sulfonates, sulfosuccinates, alkyl ether carboxylates, alkoxylated fatty acids, and alkoxylated alcohols.

Suitable pesticides are biologically active compounds used to control agricultural pests and include, for example, herbicides, plant growth regulators, crop dessicants, fungicides, bacteriocides, bacteriostats, insecticides, and insect repellants. Suitable pesticides include, for example, triazine herbicides such as metribuzin, hexaxinone, or atrazine; sulfonylurea herbicides such as chlorsulfuron; uracils such as lenacil, bromacil, or terbacil; urea herbicides such as linuron, diuron, siduron, or neburon; acetanilide herbicides such as alachlor, or metolachlor; thiocarbamate herbicides such as benthiocarb, triallate; oxadiazolone herbicides such as oxadiazon; phenoxyacetic acids such as 2,4-D; diphenyl ether herbicides such as fluazifop, acifluorfen, bifenox, or oxyfluorfen; dinitro aniline herbicides such as trifluralin; organophosphonate herbicides such as glyphosate salts and esters; dihalobenzonitrile herbicides such as bromoxynil, or ioxynil, dipyridilium herbicides such as paraquat. Suitable fungicides include, for example, nitrilo oxime fungicides such as cymoxanil; imidazole fungicides such as benomyl, carbendazim, or thiophanate-methyl; triazole fungicides such as triadimefon; sulfenamide fungicides, such as captan; dithio-carbamate fungicides such as maneb, mancozeb, or thiram; chloronated aromatic fungicides such as chloroneb; dichloro aniline fungicides such as iprodione, strobilurin fungicides such as kresoximmethyl, trifloxystrobin or azoxystrobin; chlorothalonil; copper salt fungicides such as copper oxychloride; sulfur; phenylamides; and acylamino fungicides such as metalaxyl or mefenoxam. Suitable insecticides, include, for example, carbamate insecticides, such as methomyl, carbaryl, carbofuran, or aldicarb; organo thiophosphate insecticides such as EPN, isofenphos, isoxathion, chlorpyrifos, or chlormephos; organophosphate insecticides such as terbufos, monocrotophos, or terachlorvinphos; perchlorinated organic insecticides such as methoxychlor; synthetic pyrethroid insecticides such as fenvalerate, abamectin or emamectin benzoate, neonicotinoide insecticides such as thiamethoxam or imidacloprid; pyrethroid insecticides such as lambda-cyhalothrin, cypermethrin or bifenthrin, and oxadiazine insecticides such as indoxacarb, imidachlopryd, or fipronil. Suitable miticides include, for example, propynyl sulfite miticides such as propargite; triazapentadiene miticides such as amitraz; chlorinated aromatic miticides such as chlorobenzilate, ortetradifan; and dinitrophenol miticides such as binapacryl. Suitable nematicides include carbamate nematicides, such as oxamyl.

Pesticide compounds are, in general, referred herein to by the names assigned by the International Organization for Standardization (ISO). ISO common names may be cross-referenced to International Union of Pure and Applied Chemistry ("IUPAC") and Chemical Abstracts Service ("CAS") names through a number of sources such as, for example, the *Compendium of Pesticide Common Names*, which is available on-line at http://www.hclrss.demon.co.uk/index.html.

In one embodiment, the pesticide comprises one or more compounds selected from group consisting of herbicides, plant growth regulators, crop dessicants, fungicides, bacteriocides, bacteriostats, insecticides, miticides, nematocides, and insect repellants.

In one embodiment, the pesticide comprises one or more compounds selected from the group consisting of glufosinate, glyphosate, water soluble glufosinate salts, water soluble glyphosate salts, and mixtures thereof, including, for example sodium, potassium, isopropyl amine, and ammonium salts.

In one embodiment, the pesticide comprises one or more compounds selected from the group consisting of the potassium salt of glyphosate, the sodium salt of glyphosate, the isopropyl amine salt of glyphosate, the ammonium salt of glyphosate.

Herbicidal compositions containing glyphosate or derivatives thereof are used to control a very wide variety of plants worldwide and can, when applied to the target plant in a herbicidally effective amount, reportedly control one or more target plant species of one or more of the following genera: *Abutilon, Amaranthus, Artemisia, Asclepias, Avena, Axonopus, Borreria, Brachiaria, Brassica, Bromus, Chenopodium, Cirsium, Commelina, Convolvulus, Cynodon, Cyperus, Digitaria, Echinochloa, Eleusine, Elymus, Equisetum, Erodium, Helianthus, Imperata, Ipomoea, Kochia, Lolium, Malva, Oryza, Ottochloa, Panicum, Paspalum, Phalaris, Phragmites, Polygonum, Portulaca, Pteridium, Pueraria, Rubus, Salsola, Setaria, Sida, Sinapis, Sorghum, Triticum, Typha, Ulex, Xanthium* and *Zea*, including annual broadleaf species such as, for example, velvetleaf (*Abutilon theophrasti*), pigweed (*Amaranthus* spp.), buttonweed (*Borreria* spp.), oilseed rape, canola, indian mustard, etc. (*Brassica* spp.), commelina (*Commelina* spp.), filaree (*Erodium* spp.), sunflower (*Helianthus* spp.), morningglory (*Ipomoea* spp.), kochia (*Kochia scoparia*), mallow (*Malva* spp.), wild buckwheat, smartweed, etc. (*Polygonum* spp.), purslane (*Portulaca* spp.), russian thistle (*Salsola* spp.), sida (*Sida* spp.), wild mustard (*Sinapis arvensis*) and cocklebur (*Xanthium* spp.), annual narrowleaf species such as for example, wild oat (*Avena fatua*), carpetgrass (*Axonopus* spp.), downy brome (*Bromus tectorum*), crabgrass (*Digitaria* spp.), barnyardgrass (*Echinochloa crusgalli*), goosegrass (*Eleusine indica*), annual ryegrass (*Lolium multiflorum*), rice (*Oryza sativa*), ottochloa (*Ottochloa nodosa*), bahiagrass (*Paspalum notatum*), canarygrass (*Phalaris* spp.), foxtail (*Setaria* spp.), wheat (*Triticum aestivum*) and corn (*Zea mays*), perennial broadleaf species such as, for example, mugwort (*Artemisia* spp.), milkweed (*Asclepias* spp.), canada thistle (*Cirsium arvense*), field bindweed (*Convolvulus arvensis*) and kudzu (*Pueraria* spp.), perennial narrowleaf species such as for example, brachiaria (*Brachiaria* spp.), bermudagrass (*Cynodon dactylon*), yellow nutsedge (*Cyperus esculentus*), purple nutsedge (*C. rotundus*), quackgrass (*Elymus repens*), lalang (*Imperata cylindrica*), perennial ryegrass (*Lolium perenne*), guineagrass (*Panicum maximum*), dallisgrass (*Paspalum dilatatum*), reed (*Phragmites* spp.), johnsongrass (*Sorghum halepense*) and cattail (*Typha* spp.), and other perennial species such as, for example, horsetail (*Equisetum* spp.), bracken (*Pteridium aquilinum*), blackberry (*Rubus* spp.), and gorse (*Ulex europaeus*).

As used herein, the terminology "effective amount" in reference to the relative amount of a pesticide in a pesticide composition means the relative amount of pesticide that is effective to control the growth of a target organism, for example, a target plant, fungus, bacterium, or insect, when the pesticide composition is applied to the organism at a given application rate.

In one embodiment, the pesticide is glyphosate herbicide and the pesticide composition is an herbicide composition that comprises a herbicidally effective amount of glyphosate.

As used herein, the terminology "an herbicidally effective amount" in reference to the relative amount of herbicide in an herbicidal composition means the relative amount that is effective to control growth of a target plant when the herbicidal composition is spray applied to the target plant at a given application rate.

The adjuvant composition comprises a non-zero amount of the one or more betaine surfactant compounds and a non-zero amount of one or more surfactant compounds selected from alkyl ether sulfates, sulfonates, sulfosuccinates, alkyl ether carboxylates, alkoxylated fatty acids, and alkoxylated alcohols.

In one embodiment, the pesticide composition comprises, based on 100 pbw of the adjuvant composition:
(a) greater than or equal to about 0.001 part by weight, more typically from about 0.001 pbw to about to about 0.1 pbw, even more typically from about 0.001 pbw to about 0.05 pbw, and still more typically from about 0.005 pbw to about 0.025 pbw, of one or more betaine surfactant compounds,
(b) greater than or equal to about 0.001 part by weight, more typically from about 0.001 pbw to about 0.1 pbw, even more typically from about 0.005 pbw to about 0.095 pbw, and still more typically from about 0.02 pbw to about 0.08 pbw, of one or more surfactant compounds selected from alkyl ether sulfates, sulfonates, sulfosuccinates, alkyl ether carboxylates, alkoxylated fatty acids, and alkoxylated alcohols, and
(c) an effective amount of a pesticide.

In one embodiment of the pesticide composition, the one or more surfactants comprise at least one alkyl ether sulfate surfactant and may optionally further comprise one or more surfactants selected from sulfonates, sulfosuccinates, alkyl ether carboxylates, alkoxylated fatty acids, and alkoxylated alcohols.

In one embodiment of the adjuvant composition, the one or more surfactants comprise at least one sulfonate surfactant and may optionally further comprise one or more surfactants selected from alkyl ether sulfates, sulfosuccinates, alkyl ether carboxylates, alkoxylated fatty acids, and alkoxylated alcohols.

In one embodiment of the pesticide composition, the one or more surfactants comprise at least one sulfosuccinate surfactant and may optionally further comprise one or more surfactants selected from alkyl ether sulfates, sulfonates, alkyl ether carboxylates, alkoxylated fatty acids, and alkoxylated alcohols.

In one embodiment of the pesticide composition, the one or more surfactants comprise at least one alkyl ether carboxylate surfactant and may optionally further comprise one or more surfactants selected from alkyl ether sulfates, sulfonates, sulfosuccinates, alkoxylated fatty acids, and alkoxylated alcohols In one embodiment of the pesticide composition, the one or more surfactants comprise at least one alkoxylated fatty acid surfactant and may optionally further comprise one or more surfactants selected from alkyl ether sulfates, sulfonates, sulfosuccinates, alkyl ether carboxylates, and alkoxylated alcohols In one embodiment of the pesticide composition, the one or more surfactants comprise at least one alkoxylated alcohol surfactant and may optionally further comprise one or more surfactants selected from alkyl ether sulfates, sulfonates, sulfosuccinates, alkyl ether carboxylates, and alkoxylated fatty acids.

In one embodiment, the pesticide composition comprises, based on 100 pbw of the composition, from about 10 pbw to about 90 pbw, more typically from about 30 to about 60 pbw, glyphosate.

The adjuvant and pesticide compositions of the present invention may each, optionally, further comprise one or more agronomically acceptable solvent. Suitable solvents include, for example, water, and organic solvents, such as for example, alkylated aromatic solvents, such as toluene or alkylated naphthalenes and mineral oil fractions, such as paraffinic hydrocarbons.

In one embodiment, the adjuvant composition of the present invention is an aqueous composition and thus comprises water.

In one embodiment, the pesticide composition of the present invention is an aqueous composition and thus comprises water.

In one embodiment, the adjuvant composition of the present invention further comprises, based on 100 pbw of such composition, up to about 25 pbw an organic solvent.

In one embodiment, the pesticide composition further comprises a fertilizer. Such fertilizers can provide the primary nutrients of nitrogen, phosphorus and/or potassium such as urea ammonium nitrate (30-0-0), 10-34-0, secondary nutrients sulfur, calcium, magnesium such as ammonium thiosulfate 12-0-0-26S, micronutrient fertilizers containing zinc, iron, molybdenum, copper, boron, chlorine, magnesium, for example 0-O-1 3%-S; 3%-Zn; 2%-Fe; 2%-Mn and mixtures thereof. In one embodiment, the pesticide composition comprises from about 85 to about 99 pbw, more typically from about 90 to about 99 pbw, and even more typically from about 93 to about 99 pbw, of a mixture of fertilizer and water.

In one embodiment, the pesticide composition of the present invention further comprises one or more water conditioners, such as for example, chelating agents, such as ethylenediamine tetraacetic acid, complexing agents such as ammonium sulfate, and pH adjusting agents, such as citric acid and polyacrylic acid.

In one embodiment, the pesticide composition of the present invention comprises, based on 100 pbw of such composition, from about 0.1 to about 3 pbw, more typically from about 0.7 to about 2.5 pbw, of one or more water conditioners, typically ammonium sulfate.

The pesticide composition of the present invention may, optionally, further comprise other ingredients, such as one or more additional surfactants, one or more thickeners, such as polysaccharide thickeners, and polyacrylamide thickeners, as well as antifoams, spreaders, and drift control agents.

The adjuvant composition of the present invention is made by combining and mixing the components of such composition.

The pesticide composition of the present invention is made by mixing the ingredients together. In one embodiment, the pesticide composition is made by combining and mixing the adjuvant composition of the present invention, a pesticide compound, and water. Alternatively, the pesticide composition is made by combining and mixing the separate components of the adjuvant composition, a pesticide, and water.

In one embodiment, the pesticide composition is spray applied to foliage of a target plant at a rate of from about 0.5 pint/acre to about 3 pints/acre, more typically from about 0.5 pint/acre to about 2.5 pints/acre.

Examples 1-10 and Comparative Examples C1-C4

The pesticide compositions of Examples 1-10 and Comparative Examples C1-C4 were aqueous solutions made by combining the ingredients in the relative amounts (based on 100 pbw of the respective pesticide composition) set forth below and mixing:

| EX # | Ingredients (pbw/100 pbw pesticide composition) |
|---|---|
| 1 | 1.5 pbw 30% aqueous solution of $(C_{12}-C_{14})$alkyl dimethyl betaine<br>3.5 pbw 30% aqueous solution of sodium lauryl ether sulfate, ethoxylated with 1-3 moles ethylene oxide per mole)<br>38 pbw glyphosate isopropyl amine salt (MON0139, Monsanto)<br>57 pbw water |
| 2 | 2.25 pbw 30% aqueous solution of $(C_{12}-C_{14})$alkyl dimethyl betaine<br>2.5 pbw tall oil fatty acid ethoxylated with 10 moles of ethylene oxide per mole<br>38 pbw glyphosate isopropyl amine salt (MON0139, Monsanto)<br>57.25 pbw water |
| 3 | 1.5 pbw 30% aqueous solution of $(C_{12}-C_{14})$alkyl dimethyl betaine<br>4.95 pbw tall oil fatty acid ethoxylated with 10 moles of ethylene oxide per mole<br>38 pbw glyphosate isopropyl amine salt (MON0139, Monsanto)<br>55.55 pbw water |
| 4 | 1.5 pbw 30% aqueous solution of $(C_{12}-C_{14})$alkyl dimethyl betaine<br>2.5 pbw tall oil fatty acid ethoxylated with 10 moles of ethylene oxide per mole<br>1.12 pbw 45% aqueous solution of sodium alkylphenoxy benzene sulfonate<br>38 pbw glyphosate isopropyl amine salt (MON0139, Monsanto)<br>56.88 pbw water |
| 5 | 1.5 pbw 30% aqueous solution of $(C_{12}-C_{14})$alkyl dimethyl betaine<br>2.8 pbw 56% aqueous solution of ammonium $(C_8-C_{10})$alkyl ether sulfate, ethoxylated with 3 moles ethylene oxide per mole<br>38 pbw glyphosate isopropyl amine salt (MON0139, Monsanto)<br>57.7 pbw water |
| 6 | 1.5 pbw 30% aqueous solution of $(C_{12}-C_{14})$alkyl dimethyl betaine<br>4 pbw sodium dioctyl sulfosuccinate<br>38 pbw glyphosate isopropyl amine salt (MON0139, Monsanto)<br>56.5 pbw water |
| 7 | 1.5 pbw 30% aqueous solution of $(C_{12}-C_{14})$alkyl dimethyl betaine<br>3.75 pbw sodium laureth-13 carboxylate<br>38 pbw glyphosate isopropyl amine salt (MON0139, Monsanto)<br>56.75 pbw water |
| 8 | 1.5 pbw 30% aqueous solution of $(C_{12}-C_{14})$alkyl dimethyl betaine<br>2 pbw disodium laurimide (MEA) sulfosuccinate<br>38 pbw glyphosate isopropyl amine salt (MON0139, Monsanto)<br>58.5 pbw water |
| 9 | 1.5 pbw 30% aqueous solution of $(C_{12}-C_{14})$alkyl dimethyl betaine<br>5 pbw ethoxylated (20 moles ethylene oxide per mole) oleyl alcohol<br>38 pbw glyphosate isopropyl amine salt (MON0139, Monsanto)<br>55.5 pbw water |
| 10 | 1.5 pbw 30% aqueous solution of $(C_{12}-C_{14})$alkyl dimethyl betaine<br>2 pbw ammonium xylene sulfonate<br>38 pbw glyphosate isopropyl amine salt (MON0139, Monsanto)<br>58.5 pbw water |
| C1 | 38 pbw glyphosate isopropyl amine salt (MON0139, Monsanto)<br>62 pbw water |
| C2 | 3 pbw 30% aqueous solution of $(C_{12}-C_{14})$alkyl dimethyl betaine<br>38 pbw glyphosate isopropyl amine salt (MON0139, Monsanto)<br>59 pbw water |
| C3 | 1.5 pbw 30% aqueous solution of $(C_{12}-C_{14})$alkyl dimethyl betaine<br>38 pbw glyphosate isopropyl amine salt (MON0139, Monsanto)<br>60.5 pbw water |
| C4 | Roundup ® Ultramax |

The efficacy of the compositions in controlling plant growth was tested by applying the compositions to the following plant species: Green Foxtail ("GRF"), Giant Foxtail ("GF"), Shattercane ("SC"), Barnyard Grass ("BG"), Redroot Pigweed ("PWV"), Common Waterhemp ("WH"), Common Purslane ("CP"), Kochia ("KO"), Velvetleaf ("VL"), Common Lambsquarter ("LQ"), Ivy Morning Glory ("MG"), at a rate of 0.5 pint per acre and at a rate of 1.0 pint per acre. Results for the 0.5 pint per acre application rate at 28 days post application are given in TABLE I below as percent control of plant growth for various plant species. Results for the 1.0 pint per acre application rate are given below in TABLE II as percent control of plant growth for various plant species.

TABLE I

28 Days, 0.5 pint/acre

% Control of Plant Growth

| Example # | GRF | GF | SC | BG | PW | WH | CP | KO | VL | LQ | MG |
|---|---|---|---|---|---|---|---|---|---|---|---|
| 1 | 100 | 100 | 84 | 77 | 100 | 100 | 100 | 91 | 78 | 85 | 91 |
| 2 | 100 | 100 | 91 | 83 | 100 | 100 | 73 | 72 | 68 | 88 | 91 |
| 3 | 100 | 100 | 73 | 63 | 100 | 100 | 95 | 73 | 73 | 73 | 78 |
| 4 | 100 | 100 | 79 | 62 | 100 | 100 | 88 | 71 | 42 | 78 | 91 |
| 5 | 100 | 98 | 58 | 63 | 100 | 100 | 73 | 58 | 78 | 63 | 88 |
| 6 | 100 | 99 | 58 | 68 | 100 | 100 | 78 | 63 | 30 | 58 | 86 |
| 7 | 100 | 100 | 88 | 86 | 100 | 100 | 68 | 73 | 62 | 90 | 78 |
| 8 | 100 | 100 | 73 | 72 | 100 | 100 | 78 | 58 | 28 | 73 | 81 |
| 9 | 100 | 100 | 91 | 92 | 100 | 100 | 83 | 73 | 83 | 87 | 83 |
| 10 | 100 | 100 | 81 | 74 | 100 | 100 | 83 | 63 | 73 | 81 | 71 |
| C1 | 100 | 97 | 38 | 38 | 100 | 100 | 22 | 48 | 22 | 18 | 62 |
| C2 | 100 | 100 | 78 | 73 | 100 | 100 | 73 | 73 | 48 | 82 | 63 |
| C3 | 100 | 100 | 73 | 68 | 100 | 100 | 58 | 82 | 63 | 73 | 80 |
| C4 | 100 | 100 | 73 | 82 | 100 | 100 | 78 | 92 | 72 | 85 | 48 |

TABLE II

| | 28 Days, 1.0 pint/acre |||||||||||
|---|---|---|---|---|---|---|---|---|---|---|---|
| | % Control of Plant Growth |||||||||||
| Example # | GRF | GF | SC | BG | PW | WH | CP | KO | VL | LQ | MG |
| 1 | 100 | 100 | 99 | 100 | 100 | 100 | 100 | 100 | 100 | 97 | 93 |
| 2 | 100 | 100 | 100 | 100 | 100 | 100 | 94 | 100 | 85 | 100 | 90 |
| 3 | 100 | 100 | 95 | 88 | 100 | 100 | 100 | 94 | 89 | 94 | 86 |
| 4 | 100 | 100 | 94 | 78 | 100 | 100 | 100 | 90 | 91 | 94 | 96 |
| 5 | 100 | 100 | 68 | 68 | 100 | 100 | 100 | 83 | 94 | 72 | 88 |
| 6 | 100 | 100 | 84 | 78 | 100 | 100 | 96 | 83 | 83 | 83 | 92 |
| 7 | 100 | 100 | 94 | 88 | 100 | 100 | 96 | 94 | 83 | 91 | 94 |
| 8 | 100 | 100 | 88 | 88 | 100 | 100 | 100 | 94 | 82 | 92 | 91 |
| 9 | 100 | 100 | 100 | 100 | 100 | 100 | 100 | 93 | 93 | 100 | 88 |
| 10 | 100 | 100 | 100 | 100 | 100 | 100 | 100 | 100 | 93 | 100 | 73 |
| C1 | 100 | 98 | 48 | 48 | 100 | 100 | 72 | 78 | 70 | 12 | 75 |
| C2 | 100 | 100 | 88 | 91 | 100 | 100 | 85 | 98 | 73 | 91 | 78 |
| C3 | 100 | 100 | 86 | 88 | 100 | 100 | 100 | 88 | 98 | 85 | 78 |
| C4 | 100 | 100 | 86 | 91 | 100 | 100 | 94 | 100 | 88 | 94 | 71 |

The invention claimed is:

1. A pesticide composition, comprising, based on 100 parts by weight of the composition:
   (a) greater than or equal to about 0.001 part by weight of a betaine surfactant comprising one or more compound according to formula (I):

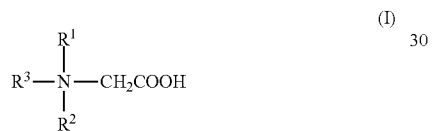

wherein $R^1$ and $R^2$ are each methyl and $R^3$ is $(C_{12}\text{-}C_{14})$alkyl,
   (b) greater than or equal to about 0.001 part by weight of one or more surfactant compounds comprising sodium lauryl ether sulfate, and
   (c) an effective amount of a pesticide comprising the isopropyl amine salt of glyphosate.

2. The composition of claim 1, wherein composition comprises, per 1 part by weight of the betaine surfactant, from about 0.1 to about 10 parts by weight of the one or more surfactant.

3. The composition of claim 1, wherein the composition further comprises one or more of agronomically acceptable solvents, fertilizers, water conditioners, chelating agents, complexing agents, pH adjusting agents, thickeners, antifoams, and drift control agents.

4. A method for treating a target plant to control the growth of the plant, comprising applying to the plant a pesticide composition according to claim 1.

* * * * *